US00PP09647P

United States Patent [19]

Williams

[11] Patent Number: Plant 9,647

[45] Date of Patent: Oct. 1, 1996

[54] SHRUB ROSE PLANT NAMED 'WILDAWN'

[76] Inventor: J. Benjamin Williams, 2800 Elnora St., Silver Spring, Md. 20902

[21] Appl. No.: 408,543

[22] Filed: Mar. 22, 1995

[51] Int. Cl.[6] ..... A01H 5/00

[52] U.S. Cl. ..... Plt./1

[58] Field of Search ..... Plt./1, 9, 7.1, 22

*Primary Examiner*—Howard J. Locker

[57] ABSTRACT

A new and distinct variety of rose plant of the shrub rose class characterized by its dwarf and compact habit of growth.

1 Drawing Sheet

BACKGROUND OF THE NEW PLANT

The present invention relates to a new and distinct variety of rose plant of the shrub class named 'Wildawn' which was originated by my crossing as seed parent 'The Fairy' (unpatented) with 'Sea Foam' (U.S. Plant Pat. No. 2,463) as the pollen parent.

Among the novel characteristics possessed by this new variety which distinguish it from its parents and all other varieties of which I am aware are its:

1. Dwarf and compact habit of growth; unlike the larger and stronger spreading habit of growth displayed by 'Sea Foam', and the low growing upright habit of 'The Fairy';

2. Good repeating blooming habit, with bloom and foliage produced in good proportion;

3. Mini-clusters of blooms borne in sprays; and

4. Above average disease resistance and excellent winter-hardiness.

Asexual reproduction by budding of the new variety as performed in McFarlin, Calif., and West Grove, Pa., shows that the foregoing and other distinguishing characteristics come true to form and are established and transmitted through succeeding propagation.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticulatural Society Colour Chart (R.H.S.C.C.). The terminology used in color description herein refers to plate numbers in the aforementioned color chart, e.g., "158-B" is plate 158-B of The Royal Horticultural Society Colour Chart.

Description of the New Variety

Flower

A. Bud:
- (1) *Size.*—Small, about 1.5 cm long when the petals start to unfurl.
- (2) *Form.*—Ovoid.
- (3) *Color.*—57-D.
- (4) *Sepals.*—Small and tight; do not extend beyond flower bud.
- (5) *Peduncle.*—Short and thin.

B. Bloom:
- (1) *Size.*—Average open size is about 3.5 cm in diameter.

- (2) *Borne.*—Compact sprays, typically made up of 15–20 blooms.
- (3) *Form.*—Open, flat, with blooms touching each other with the overall effect of forming a large decorative spray head.
- (4) *Petalage.*—Number of petals under normal conditions is 23.
- (5) *Color.*—57-D.
- (6) *Color change.*—Slight change; when first open 57-D, fully open bloom changes to 58-D.

C. Petals:
- (1) *Texture.*—Thin.
- (2) *Appearance.*—Inside velvety, outside satiny.
- (3) *Form.*—Tips slightly recurved; moderately quillted.
- (4) *Arrangement.*—Irregularly arranged, individual petals open loosely, slightly cupped.
- (5) *Petaloids in center.*—Few, not obvious when open.
- (6) *Persistence.*—Drop off cleanly.
- (7) *Fragrance.*—Slight.
- (8) *Lasting quality.*—Very long lasting, approximately 10–12 days on the plant without loss of substance.

Reproductive Organs

A. Stamens: color 13-C.
- (1) *Anthers.*—Color 9-C.
- (2) *Pollen.*—Color 13-B.

B. Pistils:
- (1) *Styles.*—Color 2-B.
- (2) *Stigmas.*—Color 14-B.

C. Hips: None observed.

Plant

A. Form: Dwarf and compact; 12–14 inches high, with a spread of 4–5 feet after 3 years.

B. Growth: Low, creeping habit.

C. Blooming habit: Good repeat bloomer.

D. Foliage:
- (1) *Size.*—Small.
- (2) *Quantity.*—Abundant, commonly 3–5 leaflets per compound leaf, 5–7 leaves develop on the main canes.
- (3) *Juvenile (new) foliage.*—Closest to 137-C. Mature foliage: Upper-side is closest to 139-A. Under-side is closest to 135-C.
- (4) *Shape.*—Oval with slight point.
- (5) *Texture.*—a) Upper side — leathery with slight waxed appearance. b) Under side — matte.
- (6) *Edge.*—Small serration.
- (7) *Serration.*—Slight.
- (8) *Leaf stem.*—Small, color closest to 137-C.
- (9) *Stipules.*—Short length; smooth.

E. Wood:

(1) *New wood.*—a) Color — 139C. b) Bark — firm and smooth.

(2) *Old wood.*—a) Color — slightly darker than 139-A. b) Bark — smooth.

F. Thorns:

(1) *Quantity.*—Very few.

(2) *Form.*—Small; curved down.

(3) *Length.*—Short (0.5 cm.).

(4) *Position.*—Irregular.

G. Prickles:

(1) *Quantity.*—Very few.

H. Plant's disease resistance:

(1) *Mildew.*—Above average.

(2) *Blackspot.*—Above average.

(3) *Rust.*—Above average.

I. Winter hardiness: Excellent.

I claim:

1. A new and distinct variety of rose plant of the shrub rose class, substantially as herein shown and described.

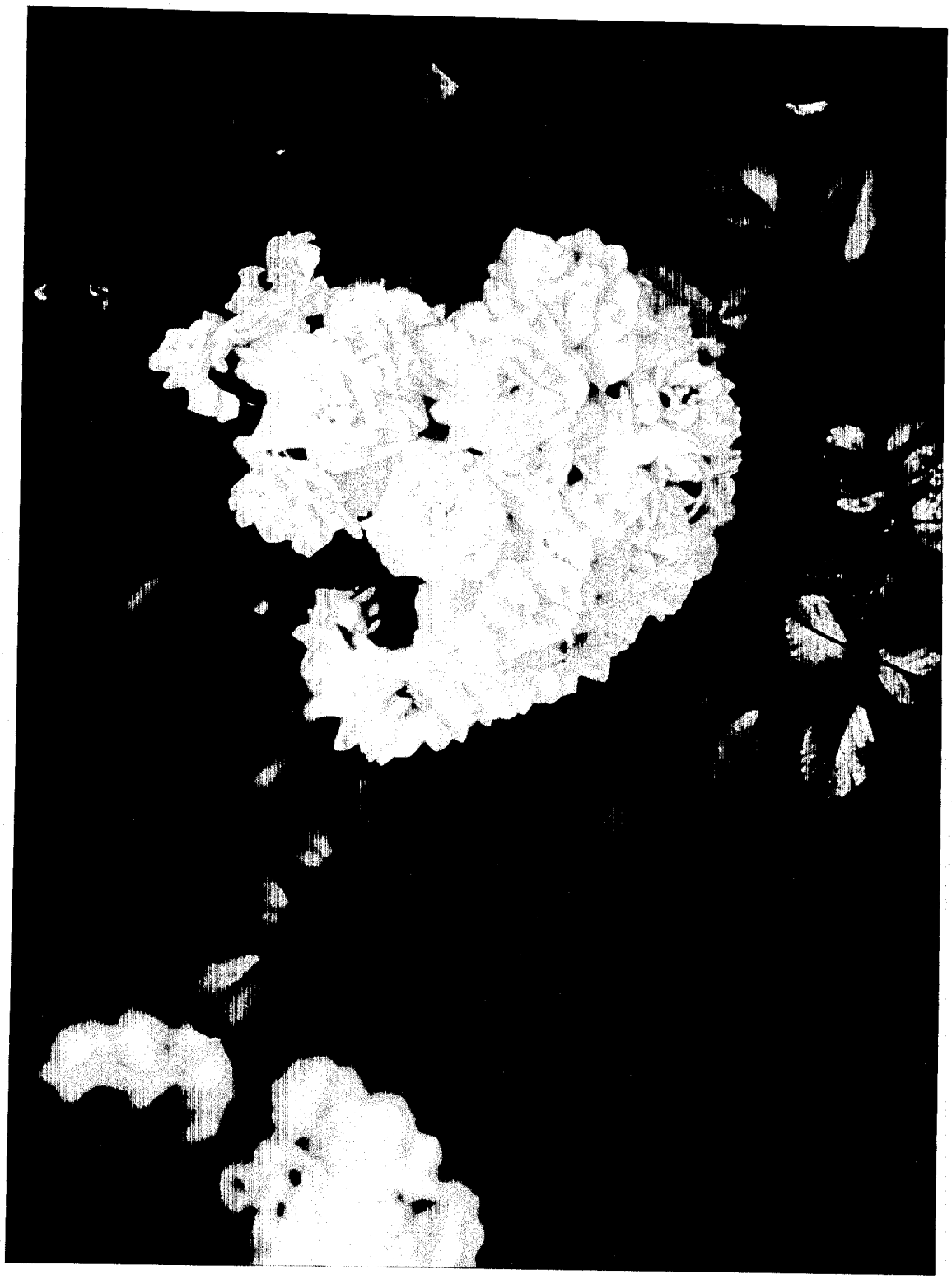

* * * * *